US009125932B2

(12) United States Patent
Ma et al.

(10) Patent No.: US 9,125,932 B2
(45) Date of Patent: Sep. 8, 2015

(54) COMPOSITION COMPRISING HERBAL EXTRACTS OR FERMENTED PRODUCTS THEREOF HAVING LACTIC ACID BACTERIA FOR PREVENTING OR TREATING RESPIRATORY DISEASES

(75) Inventors: Jin Yeul Ma, Daejeon (KR); Dong Seon Kim, Daejeon (KR); Min Cheol Yang, Gyeonggi-do (KR); Jong Hyun Yoon, Seoul (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 14/122,950

(22) PCT Filed: May 30, 2012

(86) PCT No.: PCT/KR2012/004233
§ 371 (c)(1),
(2), (4) Date: Feb. 7, 2014

(87) PCT Pub. No.: WO2012/165843
PCT Pub. Date: Dec. 6, 2012

(65) Prior Publication Data
US 2014/0140984 A1   May 22, 2014

(30) Foreign Application Priority Data
May 30, 2011 (KR) .................. 10-2011-0051653

(51) Int. Cl.
*A61K 36/00* (2006.01)
*A61K 36/725* (2006.01)
(Continued)

(52) U.S. Cl.
CPC .............. *A61K 36/725* (2013.01); *A61K 35/744* (2013.01); *A61K 36/185* (2013.01);
(Continued)

(58) Field of Classification Search
CPC ..................................... A61K 36/00
See application file for complete search history.

(56) References Cited

U.S. PATENT DOCUMENTS

2008/0031906 A1* 2/2008 Nohata et al. ................. 424/401
2010/0173024 A1* 7/2010 McDaniel ..................... 424/729

FOREIGN PATENT DOCUMENTS

KR   10-2006-0131016 A   12/2006
KR       10-0880915 B    1/2009
(Continued)

OTHER PUBLICATIONS

Search Report from International Application No. PCT/KR2012/004233 (mailed Jan. 3, 2013).

*Primary Examiner* — Rosanne Kosson
(74) *Attorney, Agent, or Firm* — Merchant & Gould P.C.

(57) ABSTRACT

The present invention relates to a composition for preventing or treating respiratory diseases, and more particularly, to a pharmaceutical composition, and to a health food, comprising extracts of herbal mixtures or fermented products thereof having lactic acid bacteria as effective ingredients for preventing or treating respiratory diseases, wherein the herbal mixtures comprise: *Sophora flavascens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix, and Polygoni cuspidati radix. The herbal extracts or fermented products thereof having lactic acid bacteria exhibit the effects of significantly lowering an airway resistance value; reducing the numbers of leukocytes, neutrophilic leukocytes, lymphocytes, eosinocytes, and basophil leukocytes to levels similar to that of a normal group; and reducing the infiltration of inflammatory cells and eosinocyte cells near AHR on lung tissues. Therefore, the herbal extracts or fermented products thereof having lactic acid bacteria may be valuably used for the prevention and/or treatment of respiratory diseases such as asthma.

8 Claims, 14 Drawing Sheets

(51) Int. Cl.
    *A61K 36/355* (2006.01)
    *A61K 36/484* (2006.01)
    *A61K 36/489* (2006.01)
    *A61K 36/185* (2006.01)
    *A61K 36/232* (2006.01)
    *A61K 36/28* (2006.01)
    *A61K 36/704* (2006.01)
    *A61K 35/744* (2015.01)
    *A61K 36/23* (2006.01)
    *A61K 36/25* (2006.01)
    *A61K 36/634* (2006.01)
    *A61K 36/78* (2006.01)

(52) U.S. Cl.
    CPC .............. *A61K 36/23* (2013.01); *A61K 36/232* (2013.01); *A61K 36/25* (2013.01); *A61K 36/28* (2013.01); *A61K 36/355* (2013.01); *A61K 36/484* (2013.01); *A61K 36/489* (2013.01); *A61K 36/634* (2013.01); *A61K 36/704* (2013.01); *A61K 36/78* (2013.01); *A61K 2236/19* (2013.01)

(56) References Cited

FOREIGN PATENT DOCUMENTS

| | | |
|---|---|---|
| KR | 10-2009-0034241 A | 4/2009 |
| KR | 10-2010-0055030 A | 5/2010 |
| KR | 10-2011-0038499 A | 4/2011 |

* cited by examiner

COMPOSITION COMPRISING HERBAL EXTRACTS OR FERMENTED PRODUCTS THEREOF HAVING LACTIC ACID BACTERIA FOR PREVENTING OR TREATING RESPIRATORY DISEASES

This application is a U.S. National Stage Application under 35 U.S.C. §371 of International Patent Application No. PCT/KR2012/004233 filed 30 May 2012, which claims the benefit of priority to Korean Patent Application No. 10-2011-0051653 filed 30 May 2011, the disclosures of all of which are hereby incorporated by reference in their entireties. The International Application was published in Korean on 6 Dec. 2012 as WO 2012/165843. To the extent appropriate, a claim of priority is made to each of the above disclosed applications.

TECHNICAL FIELD

The present invention relates to a composition for the prevention or treatment of respiratory diseases, more precisely a composition that can be effectively used for the prevention and/or treatment of respiratory diseases comprising the extract of herb mixture containing *Sophora flavascens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix, and Polygoni cuspidati radix or the fermented product thereof using lactic acid bacteria as an active ingredient.

BACKGROUND ART

Most allergic diseases are caused by the mediators (e.g. histamine, leukotrienes, TNF-α, cytokines, etc) isolated from mast cells of tissues activated by antigen-antibody reaction and neutrophils and eosinophils in blood. The recently used drugs to treat allergic diseases are just to relieve symptoms. Therefore, it is urgently requested to develop a novel drug to treat allergy more fundamentally.

Among lung diseases, asthma is a reversible obstructive airway disease which is histologically characterized by inflammatory changes. The symptoms of asthma are caused by reversible bronchoconstriction, which are exemplified by spasmodic dyspnea, cough, and sputum, etc. The development mechanism of asthma can be described by contraction or convulsion of tracheal smooth muscle, edema in bronchial mucosa, and the increase of mucus secretion, and particularly contraction of tracheal smooth muscle is most responsible for the development of asthma. The most convincing theory to explain the reason of bronchoconstriction known so far is that when an antigen is inhaled or taken, airway hypersensitivity is induced, resulting in the broad contraction of the airway. In addition, other acceptable reasons are respiratory infection, inhalation of pungent gas or air polluted by $SO_2$, heavy metal, asbestus, dust, etc., sudden change of weather, psychological stimulus, endocrine disorder, autonomic neuropathy, physical activities, and β-receptor blockade, etc. Chronic asthma and allergic asthma are well known to be the ones that can recur easily. These diseases have high risk of recurrence by cytokines of immune cells, and are known to be developed by autoimmunity.

Drugs for treating asthma are classified largely into bronchodilators, anti-inflammatory agents, and anti-allergic agents. The bronchodilator is exemplified by the material accelerating β2 adrenalin receptor. β2 adrenalin-agonist is the most representative airway muscle relaxant, which has been prescribed not only for the urgent care of asthma patients but also for the treatment of chronic asthma symptoms. β2 adrenalin-agonist increases intracellular c-AMP level by activating β2 adrenalin receptor and has the bronchodilating effect by relaxing tracheal smooth muscle.

The said β2 adrenalin-agonist is exemplified by salmeterol and formoterol, etc. These drugs demonstrate 12 hour persistence effect according to one time administration and can be administered alone or administered combined with adrenocortical hormones. In spite of high percentage of market share owing to the excellent medicinal effect, the said drugs have been restricted in prescription since a case was reported that an African American died of the abnormal increase of immune response according to the long term administration of such drugs, in addition to side effects such as palpitation, muscle crumps, and anxiety in patients. Therefore, it is requested to develop a novel drug with better medicinal effect but less side effect than the conventional β2 adrenalin-agonist.

Thus, the present inventors searched herb extracts that can be effectively used for the improvement of respiratory diseases including asthma. Particularly, the present inventors prepared herbal extracts from the herb mixture comprising *Sophora flavascens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix and Polygoni cuspidati radix, and fermented products thereof using lactic acid bacteria. And, the present inventors confirmed that the herb extracts or the fermented products thereof using lactic acid bacteria were effective in the prevention or treatment of asthma, which had never been reported before, leading to the completion of the present invention.

SUMMARY OF THE INVENTION

It is an object of the present invention to provide a composition for the prevention or treatment of respiratory diseases comprising herbal extracts or fermented products thereof using lactic acid bacteria as an active ingredient.

To achieve the above object, the present invention provides a composition for the prevention or treatment of respiratory diseases comprising herbal extracts extracted from the herb mixture comprising *Sophora flavascens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix and Polygoni cuspidati radix, or fermented products thereof using lactic acid bacteria as an active ingredient.

The present invention also provides a health food for the prevention or treatment of respiratory diseases comprising herbal extracts extracted from the herb mixture comprising *Sophora flavascens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix and Polygoni cuspidati radix, or fermented products thereof using lactic acid bacteria as an active ingredient.

DETAILED DESCRIPTION OF THE INVENTION

Description of the Preferred Embodiments

The present invention provides a composition for the prevention or treatment of respiratory diseases comprising herbal extracts extracted from the herb mixture comprising *Sophora flavascens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix and Polygoni cuspidati radix, or fermented products thereof using lactic acid bacteria as an active ingredient.

In this invention, the term "respiratory disease" indicates any disease that is developed in respiratory system such as bronchus and lung, regardless of causes either direct or indirect. In a preferred embodiment of the present invention, the respiratory disease is exemplified by asthma, bronchiectasis, chronic obstructive pulmonary disease (COPD), or chronic cough, but not always limited thereto.

The said herbal extract is preferably extracted from the herb mixture comprising 10 weight parts of *Sophora flavescens*, 2~8 weight parts of Radix glycyrrhizae, 2~8 weight parts of Flos Lonicerae, 2~8 weight parts of Angelicae Gigantis radix, 2~8 weight parts of *Aralia continentalis*, 2~8 weight parts of *Inula helenium*, 2~8 weight parts of Saposhnikoviae radix, 2~8 weight parts of *Zizyphus spinosa*, 5~15 weight parts of *Houttuynia cordata*, 2~8 weight parts of Forsythiae fructus, 5~15 weight parts of *Arctium lappa*, 2~8 weight parts of Herba epimedii, 5~15 weight parts of ginseng, 2~8 weight parts of Lithospermi radix, 2~8 weight parts of Sanguisorbae radix, 2~8 weight parts of Cnidii rhizoma, 5~15 weight parts of Scrophulariae radix, and 2~8 weight parts of Polygoni cuspidati radix. As an extraction solvent, water is generally used, but if necessary other organic solvents can be used. The usable organic solvent is exemplified by $C_1$~$C_4$ lower alcohols, acetone or its aqueous solution, but not always limited thereto. In this invention, the said "herbal extract" can be extracted from the herb mixture above not only by using water as a solvent but also by using other organic solvents.

In a preferred embodiment of the present invention, to prepare the fermented product of the herbal extract using lactic acid bacteria of the present invention (can be referred as "fermented herb" or "fermented herb extract" hereinafter), water was added to the said herb mixture at the volume of 2~15 times the mixture volume, followed by hot-water extraction at 70~130° C. to obtain a water extract. The obtained water extract was cooled down, to which lactic acid bacteria were inoculated by 0.5~5 weight %, preferably by 1 weight %. Then, the fermented herb extract of the present invention was prepared by fermenting the water extract at 20~40° C., preferably at 37° C. for 24~52 hours, preferably for 48 hours. In the case of preparing the fermented herb extract by using other organic solvents instead of water, the herbal extract needed to be dried first and then diluted in water, to which lactic acid bacteria were inoculated before fermentation.

In this invention, either an isolated lactic acid bacterial strain or a commercial lactic acid bacterial strain can be used as the lactic acid bacteria.

Particularly, *Lactobacillus* sp., *Bifidobacterium* sp., *Streptococcus* sp., *Leuconostoc* sp., *Pediococcus* sp., and *Lactococcus* sp. can be used without limitation, but among them *Lactobacillus* sp. strain is more preferred. In a preferred embodiment of the present invention, the fermented herb extract was prepared by using a variety of lactic acid bacterial strains such as *Lactobacillus rhamnosus, L. casei, L. plantarum, L. fermentum, L. bulgaricus, L. delbruekii* subsp. *lactis, L. gasseri*, and *Bifidobacterium breve* (see Example 2). However, the applicable lactic acid bacterial strain is not limited thereto, and the lactic acid bacteria culture medium can be selected from the group consisting of MRS (Man-Rogosa-Sharpe), lactose, M17, and APT (Asparagline Enrichment Broth), but not always limited thereto, either.

The herbal extract or the fermented product thereof using lactic acid bacteria of the present invention can be administered orally or parenterally and be used in general forms of pharmaceutical formulation. That is, the herbal extract or the fermented product thereof using lactic acid bacteria of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the said betaine with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The dosage unit can contain, for example, 1, 2, 3 or 4 individual doses or ½, ⅓ or ¼ of an individual dose. An individual dose preferably contains the amount of active compound which is administered in one application which usually corresponds to a whole, ½, ⅓ or ¼ of a daily dose.

The effective dosage of the herbal extract or the fermented product thereof using lactic acid bacteria of the present invention for human can be determined according to absorptiveness of the active ingredient, inactivation rate, excretion rate, age, gender, health condition and severity of a disease, etc. In general, the daily dose for adult is 10~300 mg/kg, and preferably 20~100 mg/kg, which can be administered 1~6 times a day.

In a preferred embodiment of the present invention, when the fermented product of the herbal extract of the present invention was administered to the bronchial asthma mouse model, methacholine-induced airway resistance (Penh) value was significantly lowered (see FIG. 2), compared with that of the negative control group and the comparative control group administered with the extract of ginseng, Flos Lonicerae, *Aralia continentalis*, and Radix glycyrrhizae. Both the herbal extract and the fermented product thereof using lactic acid bacteria of the present invention inhibited methacholine mediated airway resistance. Particularly, the fermented product of the herbal extract of the present invention demonstrated higher medicinal effect (see Table 3).

In another preferred embodiment of the present invention, the numbers of leukocytes, neutrophils, lymphocytes, eosinophils, and basophils were reduced to the levels similar to those of the normal group by the administration of the herbal extract or the fermented product thereof using lactic acid bacteria of the present invention (see FIG. 3~FIG. 5).

In a preferred embodiment of the present invention, the level of specific anti-OVA IgE was increased in the negative control group at least 200 times the normal group. In the group treated with the herbal extract or the fermented product thereof using lactic acid bacteria of the present invention, the level of specific anti-OVA IgE was decreased half by that of the negative control group. The levels of Th2 cytokines, IL-4 and IL-13, and TH17 cytokine, IL-17, in bronchoalveolar lavage fluid (BALF) were measured. As a result, the levels of those cytokines in bronchoalveolar lavage fluid were increased in the negative control group at least double the normal group. However, in the group treated with the herbal extract or the fermented product thereof using lactic acid bacteria of the present invention, the levels of IL-3, IL-3, and IL-17 were all reduced significantly compared with not only those in the negative control group but also those in the comparative control group administered with the extract of ginseng, Flos Lonicerae, *Aralia continentalis*, and Radix glycyrrhizae (see FIG. 6~FIG. 9).

In a preferred embodiment of the present invention, the level of IFN-γ in spleen cells was increased in the group treated with the herbal extract or the fermented product thereof using lactic acid bacteria of the present invention, compared with that in the negative control (see FIG. 10). The levels of IL-4, IL-13, and IL-17 cytokines were all significantly increased in the negative control, compared with those in the normal group, while they were reduced in the group treated with the herbal extract or the fermented product thereof using lactic acid bacteria of the present invention approximately at least 50% by the negative control group. In the meantime, in the comparative control group treated with the extract of ginseng, Flos Lonicerae, *Aralia continentalis*, and Radix glycyrrhizae, the levels of IL-4, IL-13, and IL-17 were decreased, which was though not significant compared with that of the group treated with the herbal extract or the fermented product thereof using lactic acid bacteria of the present invention (see FIG. 11~FIG. 13).

In a preferred embodiment of the present invention, histopathological test was performed with the lung tissues obtained from the bronchial asthma mouse model. As a result, in the group treated with the herbal extract or the fermented product thereof using lactic acid bacteria of the present invention, airway resistance value or lung tissue damage was inhibited, compared with that in the negative control group. Infiltration of inflammatory cells and eosinophils near AHR on lung tissues was also reduced. Bronchial/alveolar damage and collagen deposition near AHR were also inhibited in the group treated with the herbal extract or the fermented product thereof using lactic acid bacteria of the present invention, compared with the negative control group. Goblet cells around AHR were also significantly suppressed in the group treated with the herbal extract or the fermented product thereof using lactic acid bacteria of the present invention, compared with the negative control group (see FIG. 14).

The present invention also provides a health food for the prevention or alleviation of respiratory diseases comprising herbal extracts extracted from the herb mixture comprising *Sophora flavascens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix and Polygoni cuspidati radix, or fermented products thereof using lactic acid bacteria as an active ingredient.

The herbal extract or the fermented product thereof using lactic acid bacteria of the present invention can be added to health food for the prevention or treatment of respiratory diseases including asthma. In that case, the herbal extract or the fermented product thereof using lactic acid bacteria of the present invention can be added as it is or as mixed with other food components according to the conventional method. The mixing ratio of active ingredients can be regulated according to the purpose of use (prevention, health enhancement or treatment). In general, to produce health food or beverages, the herbal extract or the fermented product thereof using lactic acid bacteria of the present invention is added preferably by up to 30 weight % and more preferably by up to 10 weight %. However, if long term administration is required for health and hygiene or regulating health condition, the content can be lower than the above but higher content can be accepted as well since the herbal extract or the fermented product thereof using lactic acid bacteria of the present invention has been proved to be very safe.

The food herein is not limited. For example, the herbal extract or the fermented product thereof using lactic acid bacteria of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 g and more preferably 0.02~0.03 g in 100 and of the herbal extract or the fermented product thereof using lactic acid bacteria of the present invention.

In addition to the ingredients mentioned above, the herbal extract or the fermented product thereof using lactic acid bacteria of the present invention can include a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The herbal extract or the fermented product thereof using lactic acid bacteria of the present invention can also include fruit flesh addable to natural fruit juice, fruit beverages and vegetable beverages. All the mentioned ingredients can be added singly or together. The mixing ratio of those ingredients does not matter in fact, but in general, each can be added by 0.01~0.1 weight part per 100 weight part of the herbal extract or the fermented product thereof using lactic acid bacteria of the present invention.

Advantageous Effects

As explained hereinbefore, the herbal extracts or fermented products thereof using lactic acid bacteria exhibit the effects of significantly lowering an airway resistance value; reducing the numbers of leukocytes, neutrophils, lymphocytes, eosinophils, and basophils to the levels similar to those of a normal group; and reducing the infiltration of inflammatory cells and eosinophils near AHR on lung tissues. Therefore, the herbal extracts or fermented products thereof using lactic acid bacteria may be valuably used for the prevention and/or treatment of respiratory diseases such as asthma.

DESCRIPTION OF THE DRAWINGS

The application of the preferred embodiments of the present invention is best understood with reference to the accompanying drawings, wherein.

*$p<0.05$, $p<0.01$, *$p<0.001$

Figure 3:
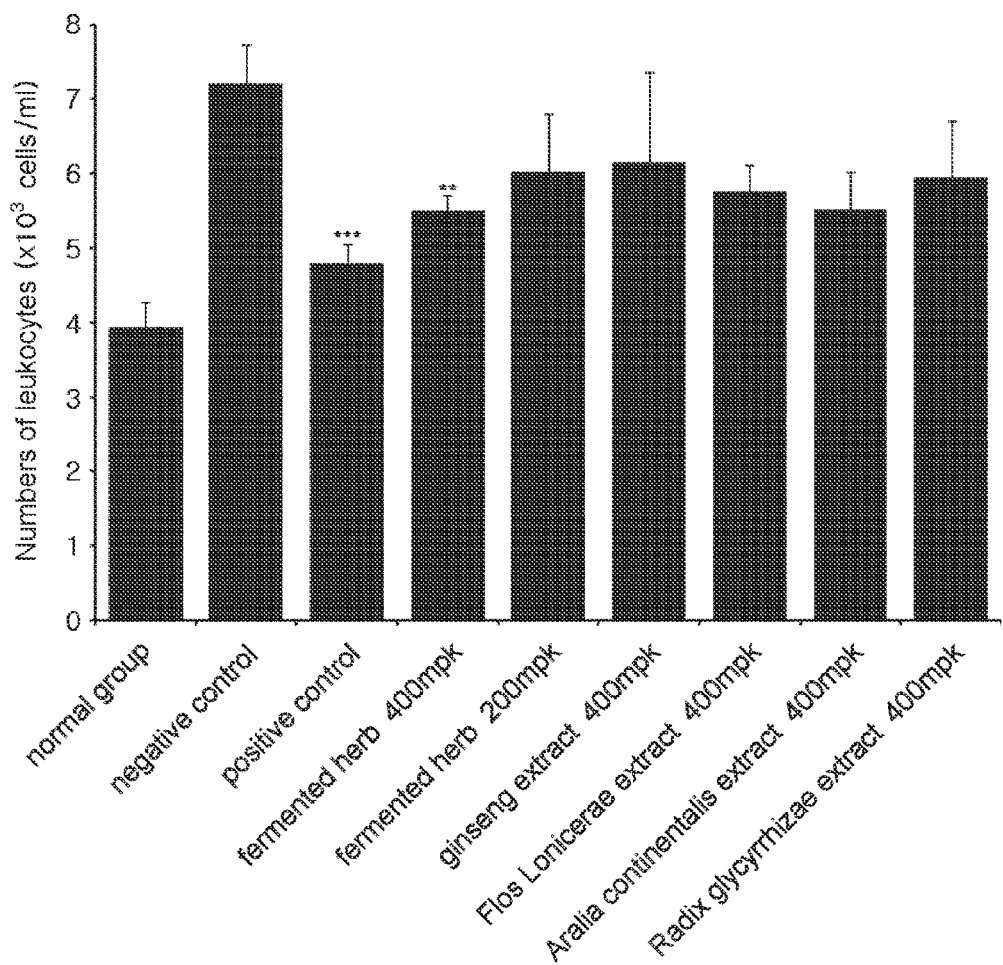
Figure 4:
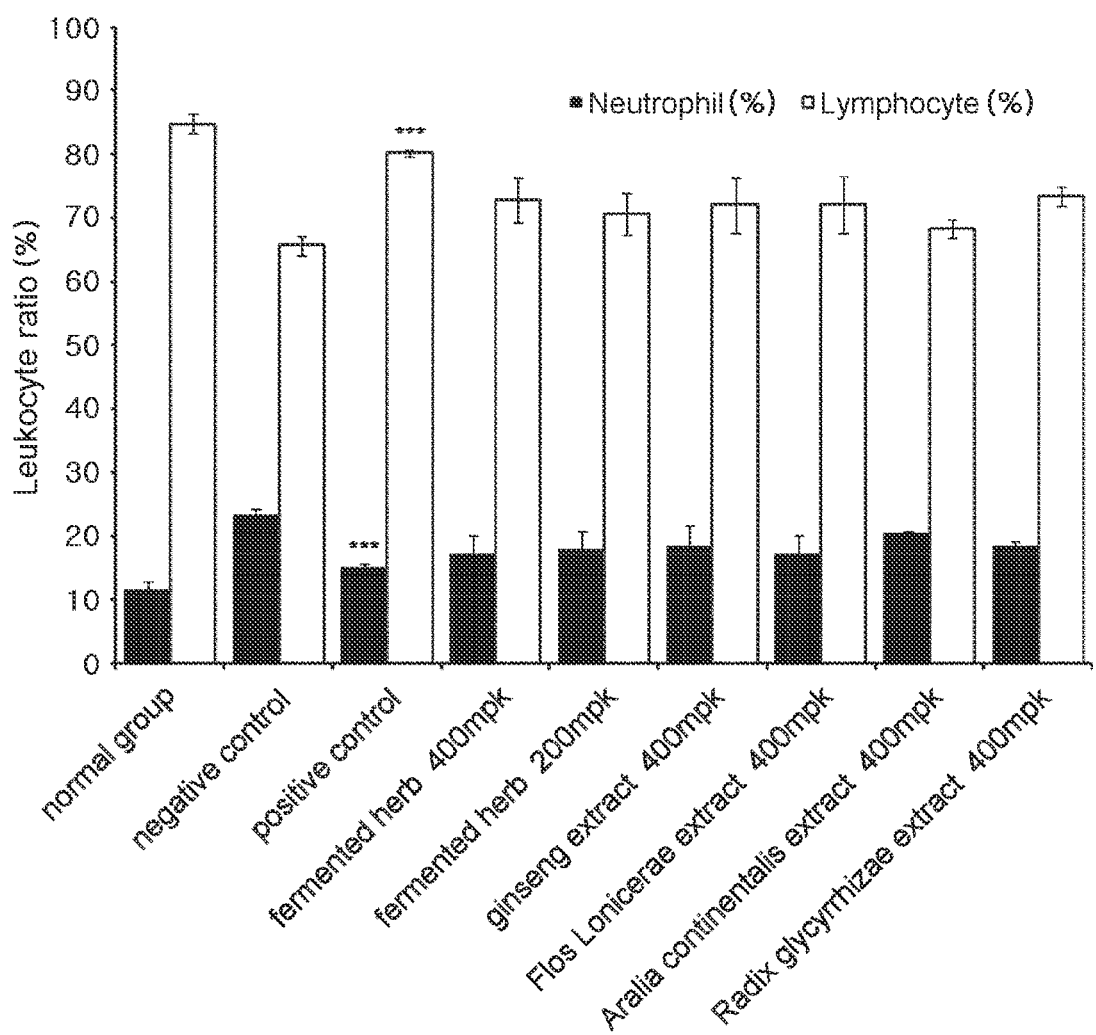
Figure 5:
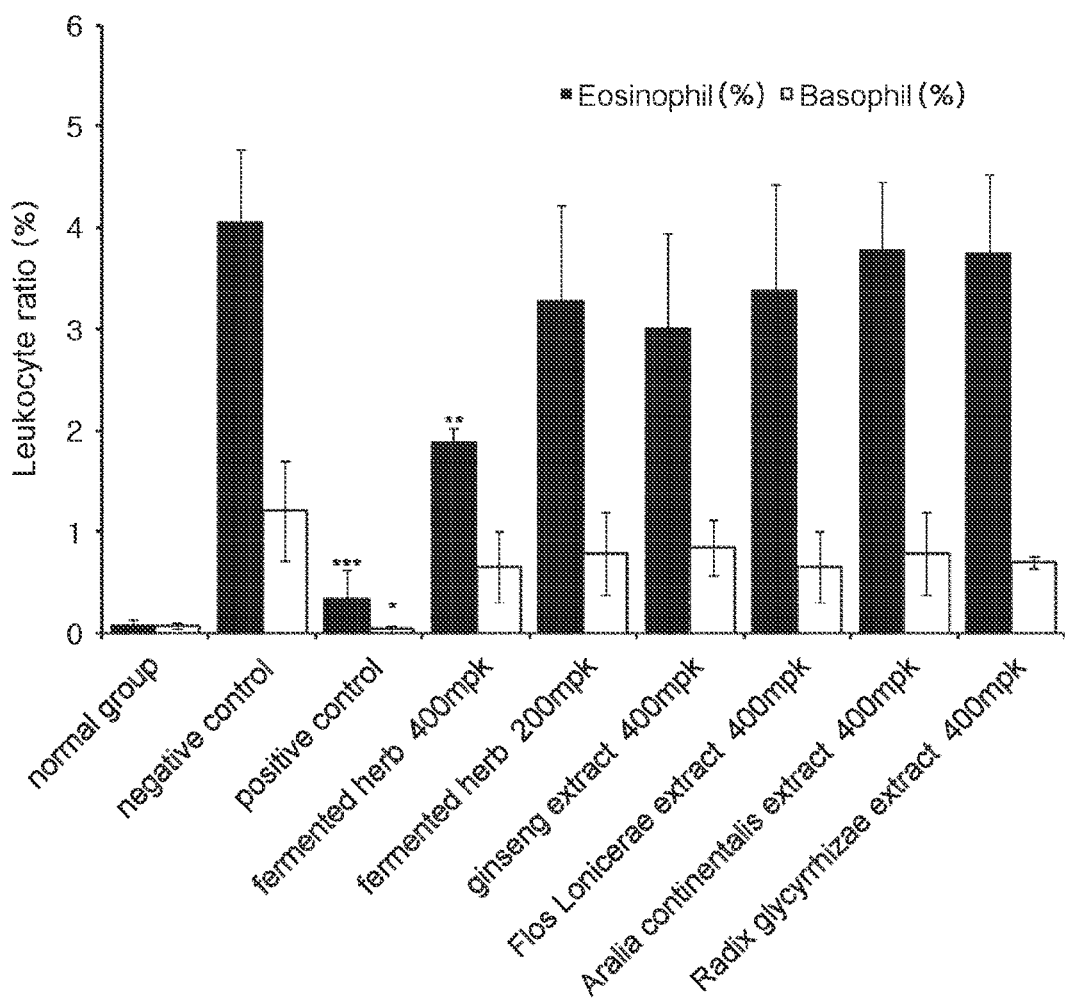

FIG. 3~FIG. 5 are graphs illustrating the numbers of leukocytes, neutrophils, lymphocytes, eosinophils, and basophils in blood.

*$p<0.05$, $p<0.01$, *$p<0.001$

FIG. 6~FIG. 9 are graphs illustrating the effect of the fermented product of the herbal extract using lactic acid bacteria of the present invention on the levels of various cytokines in the bronchoalveolar lavage fluid, in which the concentrations of OVA IgE (FIG. 6), IL-4 (FIG. 7), IL-13 (FIG. 8), and IL-17 (FIG. 9) in the bronchoalveolar lavage fluid were shown.

*$p<0.05$, $p<0.01$, *$p<0.001$

FIG. 10~FIG. 13 are graphs illustrating the effect of the fermented product of the herbal extract using lactic acid bacteria of the present invention on the levels of various cytokines in spleen cells, in which the concentrations of OVA IgE (FIG. 10), IL-4 (FIG. 11), IL-13 (FIG. 12), and IL-17 (FIG. 13) in spleen cells were showed.

*$p<0.05$, $p<0.01$, *$p<0.001$

Figure 14:
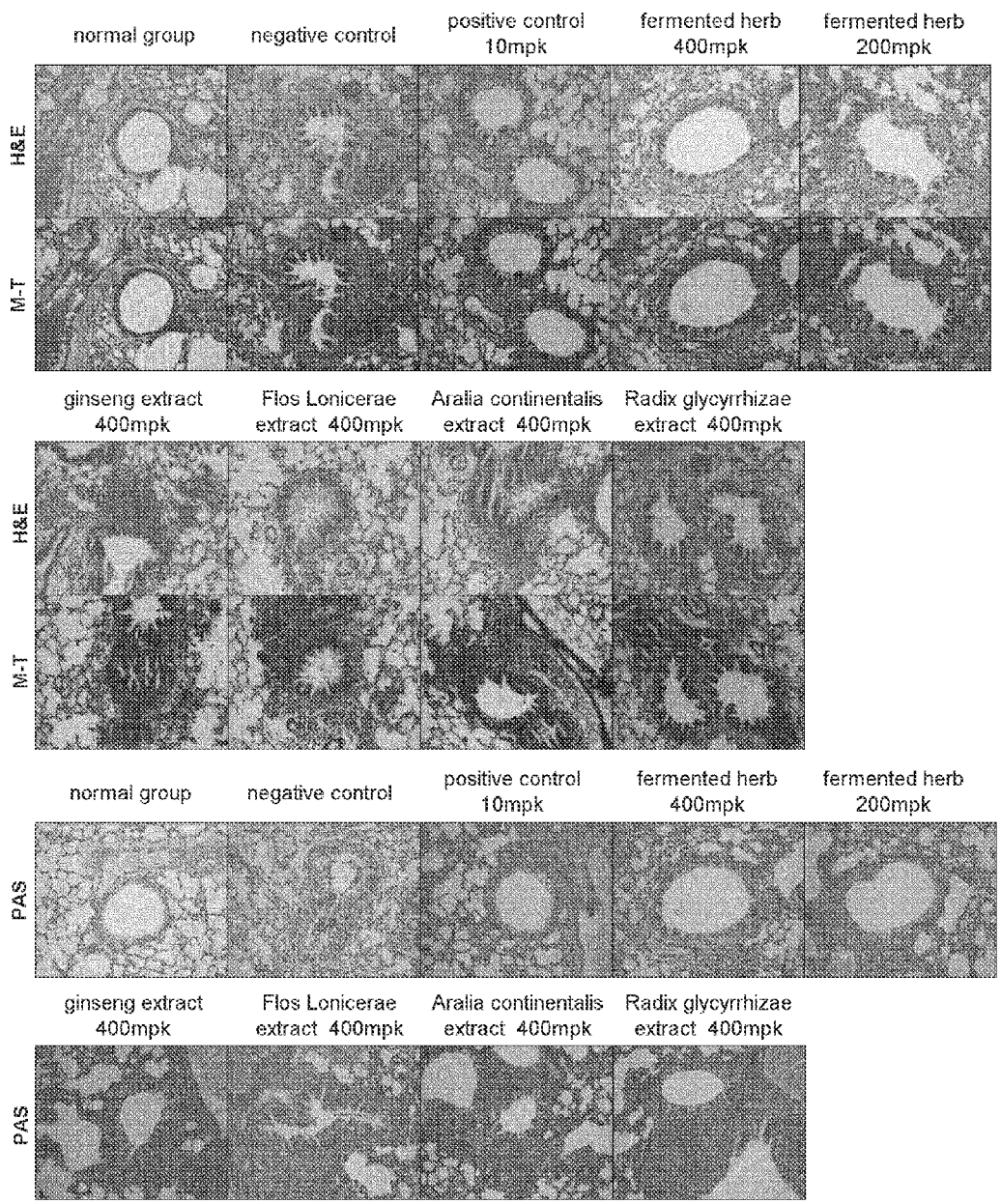

FIG. 14 is a set of photographs illustrating the results of H&E, M-T, and PAS pictures illustrating the result of the histopathological tests with the lung tissues. The normal group, the negative control group, the positive control group (CsA treated group), the group treated with the fermented product of the herbal extract using lactic acid bacteria of the present invention, and the group treated with the extract of ginseng, Flos Lonicerae, *Aralia continentalis* and Radix glycyrrhizae were stained with H&E, M-T, and PAS.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Herbal Extract

The herbal extract of the present invention is an Oriental pharmaceutical preparation which was prepared by extracting the herb mixture composed of *Sophora flavescens*, Radix glycyrrhizae, Flos Lonicerae, Angelicae Gigantis radix, *Aralia continentalis, Inula helenium*, Saposhnikoviae radix, *Zizyphus spinosa, Houttuynia cordata*, Forsythiae fructus, *Arctium lappa*, Herba epimedii, ginseng, Lithospermi radix, Sanguisorbae radix, Cnidii rhizoma, Scrophulariae radix, and Polygoni cuspidati radix. Particularly, the herb mixture was prepared with 160 g of *Sophora flavescens*, 80 g of Radix glycyrrhizae, 80 g of Flos Lonicerae, 80 g of Angelicae Gigantis radix, 80 g of *Aralia continentalis*, 80 g of *Inula helenium*, 80 g of Saposhnikoviae radix, 80 g of *Zizyphus spinosa*, 160 g of *Houttuynia cordata*, 80 g of Forsythiae fructus, 160 g of *Arctium lappa*, 80 g of Herba epimedii, 160 g of ginseng, 80 g of Lithospermi radix, 80 g of Sanguisorbae radix, 80 g of Cnidii rhizoma, 160 g of Scrophulariae radix, and 80 g of Polygoni cuspidati radix. The herb mixture in the total volume of 1,840 g was mixed with 18.4 l of distilled water (10 times the volume of the mixture), which stood for 1 hour for immersion, followed by extraction using a high-speed vacuum extractor (cosmos-600, Kyungseo Machine, Korea) at 115° C. for 3 hours. The obtained extract was filtered with standard testing sieve (Aperture 500 μm and 150 μm). As a result, the herbal extract of the present invention was prepared.

Example 2

Preparation of Fermented Product of Herbal Extract Using Lactic Acid Bacteria

<2-1> Seed Culture of Lactic Acid Bacteria

Lactic acid bacteria used for the preparation of the fermented product of the herbal extract using lactic acid bacteria of the present invention are as follows: *Lactobacillus rhamnosus* (KFRI #128), *L. casei* (KFRI #127), *L. plantarum* (KFRI #144, KFRI #402), *L. fermentum* (KFRI #164), *L. bulgaricus* (KFRI #344), *L. delbruekii* subsp. *Lactis* (KFRI #442), *L. gasseri* (KFRI #658, KCTC 3163), and *Bifidobacterium breve* (KFRI #744). The said strains were sub-cultured on slant medium and in liquid medium, being prepared for the experiments. Particularly, lactic acid bacteria were inoculated on slant medium, followed by culture at 37° C., for 24 hours. Once colonies were formed, oxygen was blocked by using paraffin film. The slant medium was then stored in a refrigerator. To prevent the strain from losing its activity or from being contaminated with other bacteria, the colonies were inoculated on fresh slant agar medium every 2~3 weeks. Then, the colonies were inoculated in liquid medium, followed by culture at 37° C., for 24 hours. MRS medium (10 g/l Peptone, 10 g/l Beef extract, 5 g/l Yeast extract, 20 g/l Glucose, 1 ml/l Tween 80, 2 g/l $K_2HPO_4$, 5 g/l Sodium acetate, 2 g/l Triammonium citrate, 0.2 g/l $MgSO_4.7H_2O$, 0.2 g/l $MnSO_4.4H_2O$, pH 6.2-6.6) was used for the seed culture.

<2-2> Fermentation of Herbal Extract Using Lactic Acid Bacteria pH of the herbal extract prepared in Example 1 was adjusted to 8.0 by using 1M NaOH, and the extract was autoclaved (121° C., 1.5 atm, 15 min), which was then cooled down to room temperature. Before fermentation, pH of the control was lowered to 6.3 from 8.0. This was because some of dietary fibers included in the herbal extract were decomposed and turned to organic acid under the high-temperature high-pressure condition (121° C., 1.5 atm, 15 min). The said lactic acid bacteria (1-5×10$^8$ CFU/ml) were added to the herbal extract at the volume of 1% (v/v), followed by aeration culture at 37° C. for 48 hours, leading to liquid fermentation. The culture solution was then filtered with standard testing sieve. As a result, the fermented product of the herbal extract using lactic acid bacteria of the present invention was prepared. The changes of dry weight and pH of the fermented product of the herbal extract using lactic acid bacteria of the present invention were as shown in Table 1.

TABLE 1

|  | pH | Dry weight (%) |
|---|---|---|
| Control | 6.19 ± 0.00 | 2.97 ± 0.02 |
| KFRI 127 | 4.42 ± 0.01 | 3.02 ± 0.01 |
| KFRI 128 | 4.00 ± 0.01 | 2.97 ± 0.03 |
| KFRI 144 | 4.26 ± 0.00 | 2.97 ± 0.02 |
| KFRI 164 | 4.52 ± 0.00 | 3.04 ± 0.00 |
| KFRI 344 | 4.36 ± 0.01 | 3.06 ± 0.01 |
| KFRI 402 | 4.34 ± 0.01 | 3.02 ± 0.02 |
| KFRI 442 | 4.03 ± 0.01 | 3.02 ± 0.00 |
| KFRI 658 | 4.65 ± 0.01 | 2.88 ± 0.04 |
| KFRI 744 | 3.84 ± 0.01 | 2.88 ± 0.00 |
| KCTC 3163 | 4.25 ± 0.01 | 3.00 ± 0.02 |

From the above results, it was confirmed that pH of the herbal extract was lowered to 4.0 by the lactic acid bacteria fermentation, indicating active acid producing capability therein. The fermented product of the herbal extract using lactic acid bacteria of the present invention was freeze-dried and stored at 4° C. until use.

<2-3> Analysis of Fermented Product of Herbal Extract

Residue in the fermented product of the herbal extract using lactic acid bacteria of the present invention prepared above was eliminated by centrifugation, which was then filtered with 0.45 μm filter. HPLC was performed under the conditions shown in Table 2.

TABLE 2

| Column | | Reversed Phase Column ($C_{18}$, 250 × 4.6 mm, 5 μm) |
|---|---|---|
| Detecter | | UV 254 nm |
| Solvent | A | 2% acetic acid |
|  | B | Acetonitrile |
| Running Time | | 65 min |
| Loading Volume | | 20 μl |
| Flow Rate | | 1.0 ml/min |

| Density Gradient Table | |
|---|---|
| Time | A/B |
| 0 | 80/20 |
| 5 | 80/20 |
| 50 | 20/80 |
| 55 | 80/20 |
| 65 | 80/20 |

Figure 1:
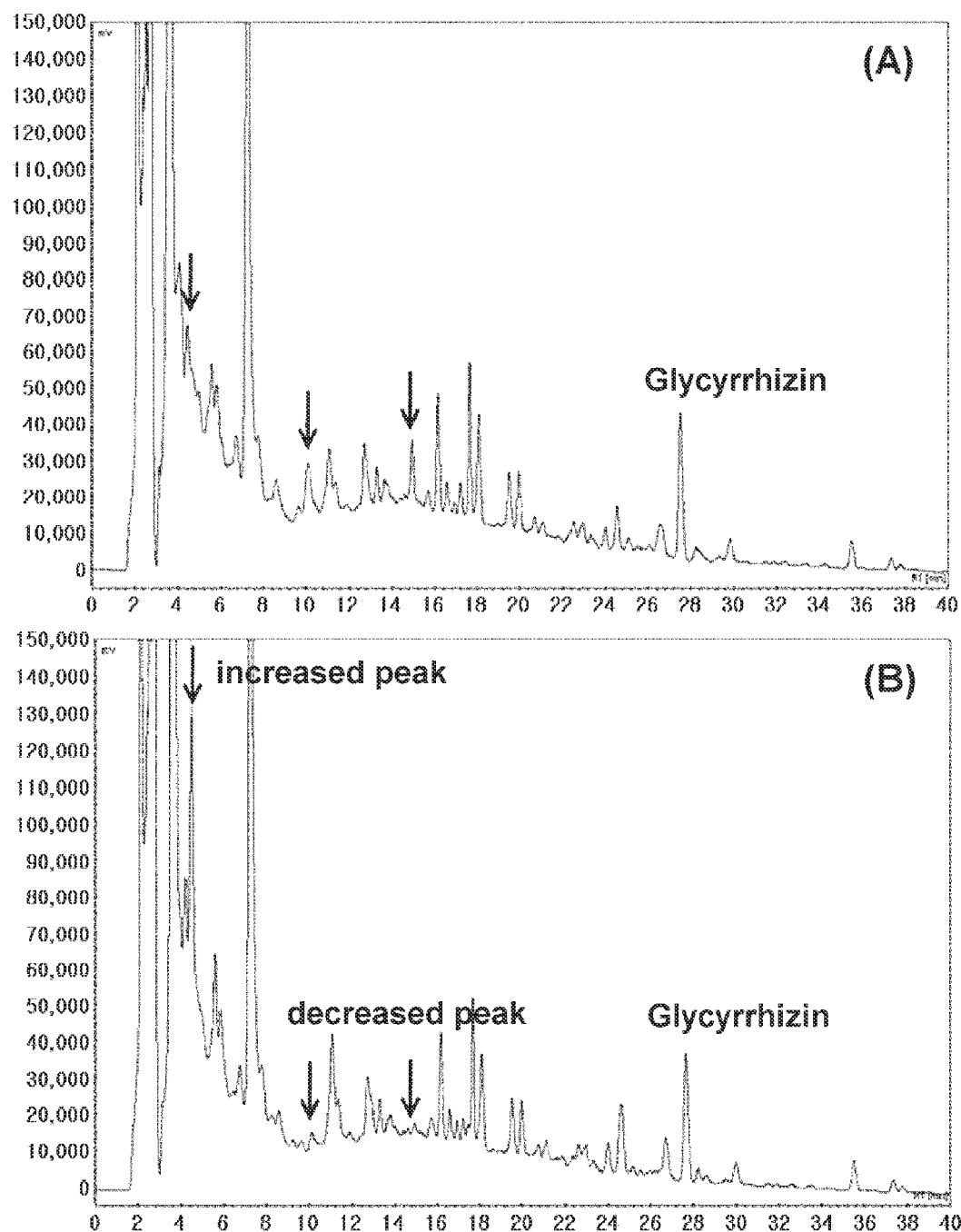
FIG. 1 is a diagram showing the chromatograms of the herbal extract (A) and the fermented product thereof using lactic acid bacteria (B) of the present invention.

As a result, in the case of the herbal extract fermented by *Lactobacillus rhamnosus* (KFRI #128), the peak at the time point of 4.5 min. was 4.3 fold increased, compared with that of the herbal extract not fermented. In the meantime, the peaks at the time points of 10.1 min. and 14.9 min. were decreased with fermentation (68% and 79% respectively). Glycyrrhizin (27.5 min.), one of the important index materials for the herbal extract of the present invention, was detected both before and after the fermentation using lactic acid bacteria (FIG. 1). Following experiments were performed with the fermented product of the herbal extract by *Lactobacillus rhamnosus* (KFRI #128).

Comparative Example 1

Preparation of ginseng, Flos Lonicerae, *Aralia continentalis*, and Radix glycyrrhizae extracts 1 kg of ginseng, Flos Lonicerae, *Aralia continentalis*, or Radix glycyrrhizae was mixed with 10 l of distilled water, which stood for 1 hour for immersion, followed by extraction using a high-speed vacuum extractor (cosmos-600, Kyungseo Machine, Korea) at 115° C. for 3 hours. The obtained extract was filtered with standard testing sieve (Aperture 500 μm and 150 μm). As a result, four different herbal extracts were prepared.

Experimental Example 1

Establishment of Bronchial Asthma Mouse Model

500 μg/ml ovalbumin (OVA, chicken egg ovalbumin; Grade IV) and 10% Alum (aluminum potassium sulfate; Sigma) (w/v) were dissolved in PBS and mixed. pH of the mixture was adjusted to 6.5 by using 10 N NaOH. Then, the mixture stood at room temperature for 1 hour, followed by centrifugation at 750×g for 5 minutes. Distilled water was added to the obtained OVA/Alum pellet until the pellet was dissolved and the solution volume reached the original volume. The mouse model was administered with OVA/Alum (100 μg/0.2 ml) via intraperitoneal injection on day 0 and day 7 for systemic sensitization. After the first intraperitoneal injection with OVA/Alum (day 0), the mouse was anesthetized on day 4 and day 14, to which 100 μl of 2% OVA was treated by intratrachial administration (i.t). On the third week, 1% OVA solution was sprayed by using a nebulizer, for 30 minutes a day, three times a week, to let the mouse inhale thereof through the nasal cavity and the airway. Blood was taken from the eyeballs. Then, the level of anti-OVA antibody level in blood was measured to select the OVA asthma model mouse.

Experimental Example 2

Measurement of Methacholine-Induced Airway Resistance Value (Pehn)

From the fourth week of systemic sensitization performed in Experimental Example 1, the mouse was inhaled with 1% OVA solution for 3 weeks and 2% OVA solution for 1 week, for 30 minutes per day, three times a week. From the fourth week, the mouse was administered with the fermented product of the herbal extract using lactic acid bacteria prepared in Example 2 (400 mpk or 200 mpk) or the extracts of ginseng, Flos Lonicerae, *Aralia continentalis* and Radix glycyrrhizae prepared in Comparative Example 1 (400 mpk) and inhaled with OVA solution for 4 weeks. For the last 1 week, 2% OVA solution was sprayed, and then methacholine (MCH) induced airway resistance value was measured. 300 mpk of the herbal extract prepared in Example 1 and 300 mpk of the fermented product of the herbal extract prepared in Example 2 were also treated by the same manner as described above, followed by measurement of methacholine induced airway resistance value. Particularly, test animals which were not anesthetized were placed in systemic chamber, where 3.125, 6.25, 12.5, 25, and 50 mg/me of MCH were inhaled. Then, methacholine induced airway resistance value was measured by flow transducer. In this experimental example, the fermented product of the herbal extract of the present invention, CsA, and the extracts of Flos Lonicerae, *Aralia continentalis*, and Radix glycyrrhizae (the positive control materials) were suspended in distilled water before use. Results obtained from different experiments were presented by mean±standard error. Statistical significance was evaluated by using Student's T-test.

Figure 2:
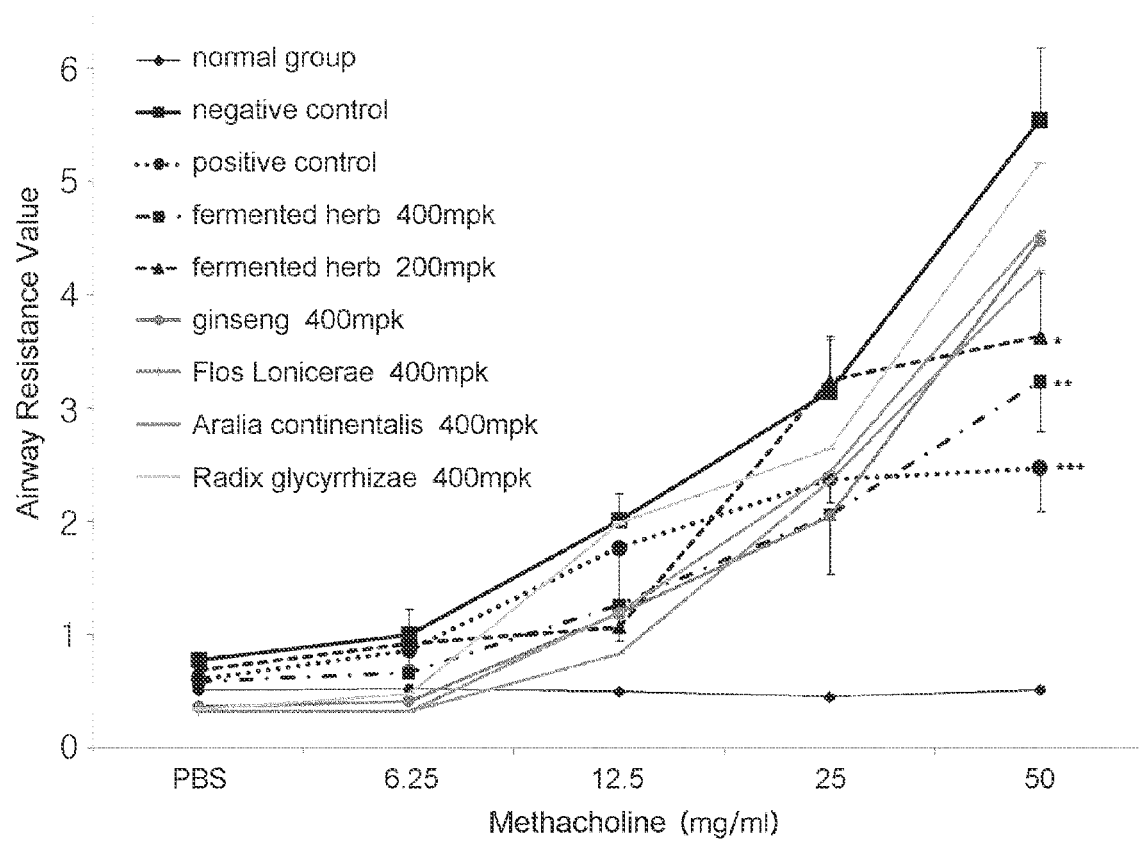
FIG. 2 is a graph illustrating the effects of the fermented product of the herbal extract using lactic acid bacteria of the present invention, Cyclosporin A (CsA), the positive control, and other extracts of Flos Lonicerae, *Aralia continentalis*, and Radix glycyrrhizae, on methacholine-induced AHR.

As a result, in the negative control group treated with OVA only, the airway resistance value induced by 50 mg/ml of MCH was about 5.547±0.64, which was significantly increased compared with that of the normal group (0.517±0.03, wide type). In the positive control group treated with 10 mpk of CsA, the airway resistance value induced by 50 mg/ml of MCH was 2.480±0.377, which was inhibited approximately 55.3% by the negative control group (P<0.001). In the group treated with the fermented product of the herbal extract of the present invention at the concentration of 400 mpk and 200 mpk respectively, the methacholine induced airway resistance values were respectively 3.236±0.44 and 3.633±0.56, suggesting that airway resistance was suppressed respectively 41.7% and 34.5% by the negative control (p<0.01, p<0.05). In the meantime, in the groups treated with the extracts of ginseng, Flos Lonicerae, *Aralia continentalis* and Radix glycyrrhizae at the concentration of 400 mpk, the methacholine induced airway resistance values were respectively 4.48±1.02, 4.211±0.50, 4.56±0.50, and 5.173±0.67, suggesting that the airway resistance value was rather reduced, compared with that of the negative control. However, the effect was significantly lower than that of the fermented product of the herbal extract of the present invention (FIG. 2). Methacholine induced airway resistance was also measured in the groups treated with the herbal extract prepared in Example 1 and the fermented product of the herbal extract prepared in Example 2 at the concentration of 300 mpk. As a result, methacholine induced airway resistance was suppressed in both groups treated with the herbal extract and the fermented product thereof, compared with that of the negative control group. Particularly, the inhibitory effect was higher when the fermented product of the herbal extract of the present invention was treated (Table 3).

TABLE 3

| | Amount of methacholine inhaled (mg/ml) | | | | |
| --- | --- | --- | --- | --- | --- |
| | PBS | 6.25 | 12.5 | 25 | 50 |
| Normal Group | 0.474 ± 0.02 | 0.633 ± 0.07 | 1.241 ± 0.15 | 2.164 ± 0.11 | 2.120 ± 0.23 |
| Negative Control | 0.500 ± 0.03 | 1.453 ± 0.24 | 3.378 ± 0.33 | 4.253 ± 0.39 | 5.978 ± 0.46 |
| Positive Control (CsA 10 mpk) | 0.470 ± 0.04 | 0.844 ± 0.07 | 1.519 ± 0.30 | 2.016 ± 0.29 | 2.947 ± 0.05 |
| Herbal Extract | 0.502 ± 0.03 | 0.844 ± 0.05 | 1.802 ± 0.24 | 3.817 ± 0.28 | 4.059 ± 0.37 |
| Fermented Product | 0.653 ± 0.04 | 0.756 ± 0.16 | 0.967 ± 0.05 | 2.519 ± 0.50 | 3.432 ± 0.40 |

Experimental Example 3

Blood Analysis (Hematology)

Upon completion of the experiment, 0.5 and of heart blood was taken by using a heparin (20 i.U) treated tube type syringe. The blood sample was sent to Biotoxtech Co. Ltd. (Cheongju, Chungcheongbuk-do, Korea) to measure the total cell numbers of leukocytes, neutrophils, lymphocytes, eosinophils, and basophils. Particularly, the number of leukocytes was measured by using an automatic blood cell counter (MS9-5, MELET SCHLOESING, France) with Minos-ST according to the method of Fonio (Fonio, A. (1912). Dtsch. Z. Chir., 117, 176.).

As a result, the ratio of leukocytes in the negative control, upon completion of the experiment, was increased at least twice the normal group, while the ratio of leukocytes in the positive control group treated with CsA was reduced almost to the level of normal group (p<0.001). The ratio of leukocytes in the groups treated with the fermented product of the herbal extract of the present invention, and the extracts of ginseng, Flos Lonicerae, *Aralia continentalis* and Radix glycyrrhizae was all reduced, compared with that of the negative control group (FIG. 3). The ratio of neutrophils was increased in the negative control group, compared with that of the normal group, but reduced in the positive control group treated with CsA close to the level of the normal group (p<0.001). The ratio of neutrophils in the groups treated with the fermented product of the herbal extract of the present invention, and the extracts of ginseng, Flos Lonicerae, *Aralia continentalis* and Radix glycyrrhizae was all reduced, compared with that of the negative control group. The ratio of lymphocytes was reduced in the negative control group, compared with that of the normal group, but increased in the positive control group treated with CsA close to the level of the normal group (p<0.001). The ratio of lymphocytes in the groups treated with the fermented product of the herbal extract of the present invention, and the extracts of ginseng, Flos Lonicerae, *Aralia continentalis* and Radix glycyrrhizae was all increased, compared with that of the negative control group (FIG. 4). The ratio of eosinophils was increased in the negative control group, compared with that of the normal group, but reduced in the positive control group treated with CsA close to the level of the normal group (p<0.005). The ratio of eosinophils in the groups treated with the fermented product of the herbal extract of the present invention, and the extracts of ginseng, Flos Lonicerae, *Aralia continentalis* and Radix glycyrrhizae was all reduced, compared with that of the negative control group. The ratio of basophils was significantly increased in the negative control group, compared with that of the normal group, but reduced in the positive control group treated with CsA close to the level of the normal group (p<0.05). The ratio of basophils in the groups treated with the fermented product of the herbal extract of the present invention, and the extracts of ginseng, Flos Lonicerae, *Aralia continentalis* and Radix glycyrrhizae was all reduced, compared with that of the negative control group (FIG. 5).

Experimental Example 4

ELISA

ELISA (enzyme-linked immuno-sorbent assay, Shibayagi, Japan) was performed to measure the levels of anti-OVA IgE, IFN-γ, IL-4, IL-13, and IL-17 in serum, BALF, and culture fluid of spleen cells extracted from the asthma mouse model. Particularly, each antibody was diluted in coating buffer, with which microwell plate was coated. The well plate stood at 4° C. for overnight. Each well of the plate was washed with washing buffer three times, to which 100 μl of serum (10-fold diluted) was distributed. The well plate stood at room temperature for 1 hour, followed by washing with washing buffer twice. 100 μl of antibody avidin-HRP conjugate was treated thereto, which stood at room temperature for 1 hour and then washed. 100 μl of TMB substrate was distributed into each well of the plate, which stood in the darkness for 30 minutes. 50 μl of stop solution was added to each well of the plate. Then, $OD_{450}$ was measured with an ELISA reader.

Figure 6:
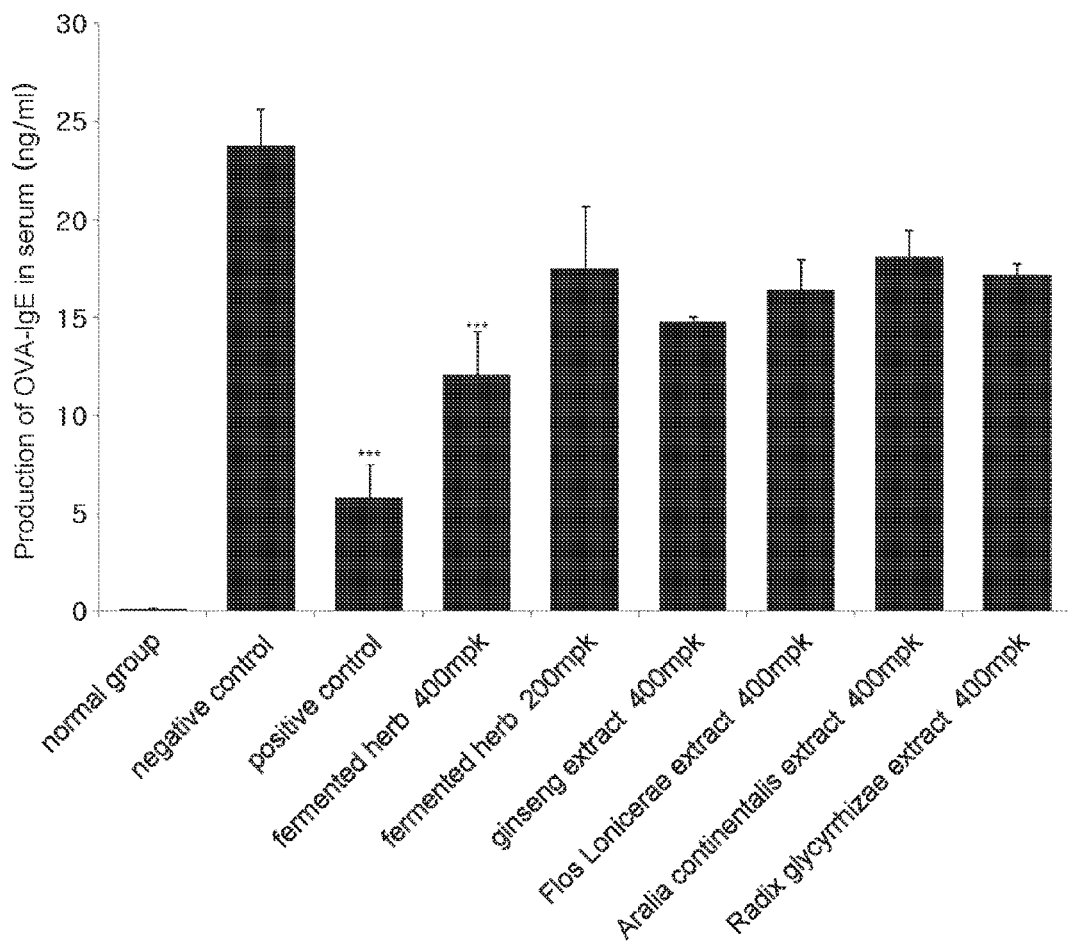
Figure 7:
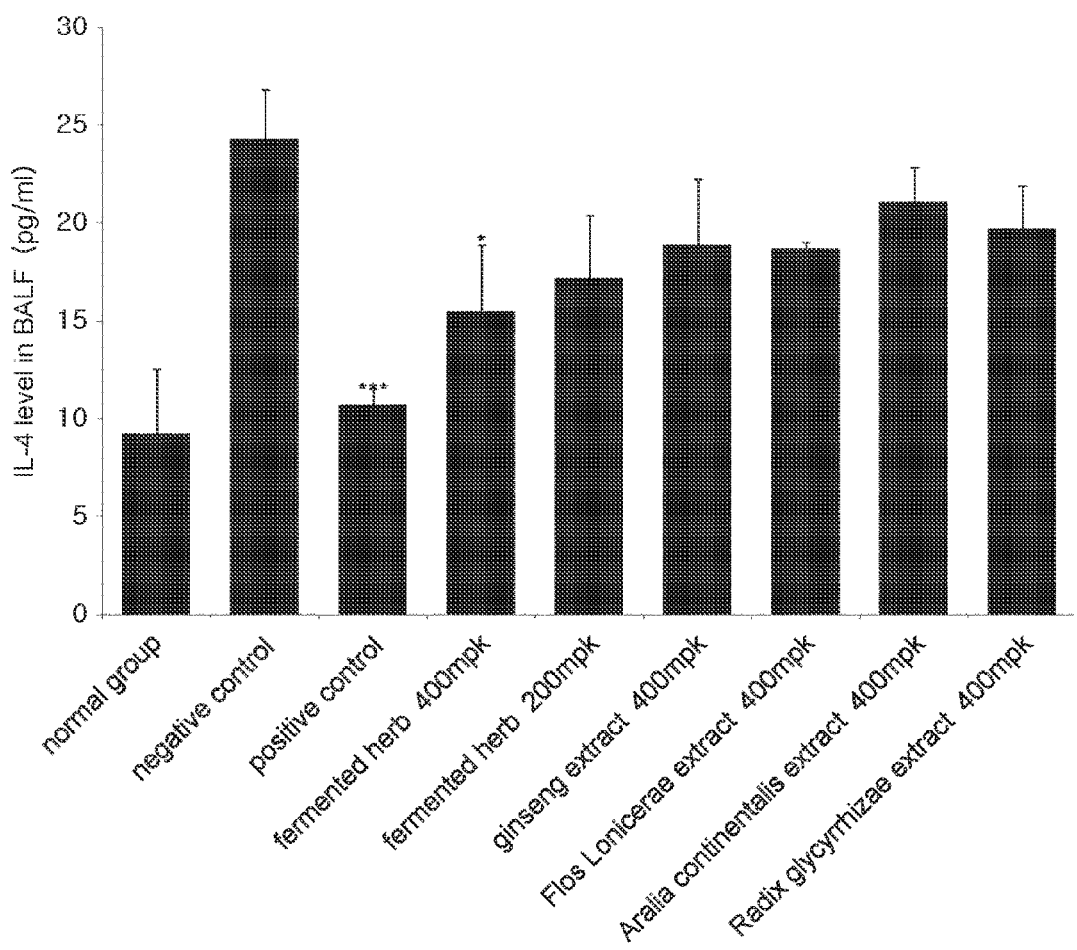
Figure 8:
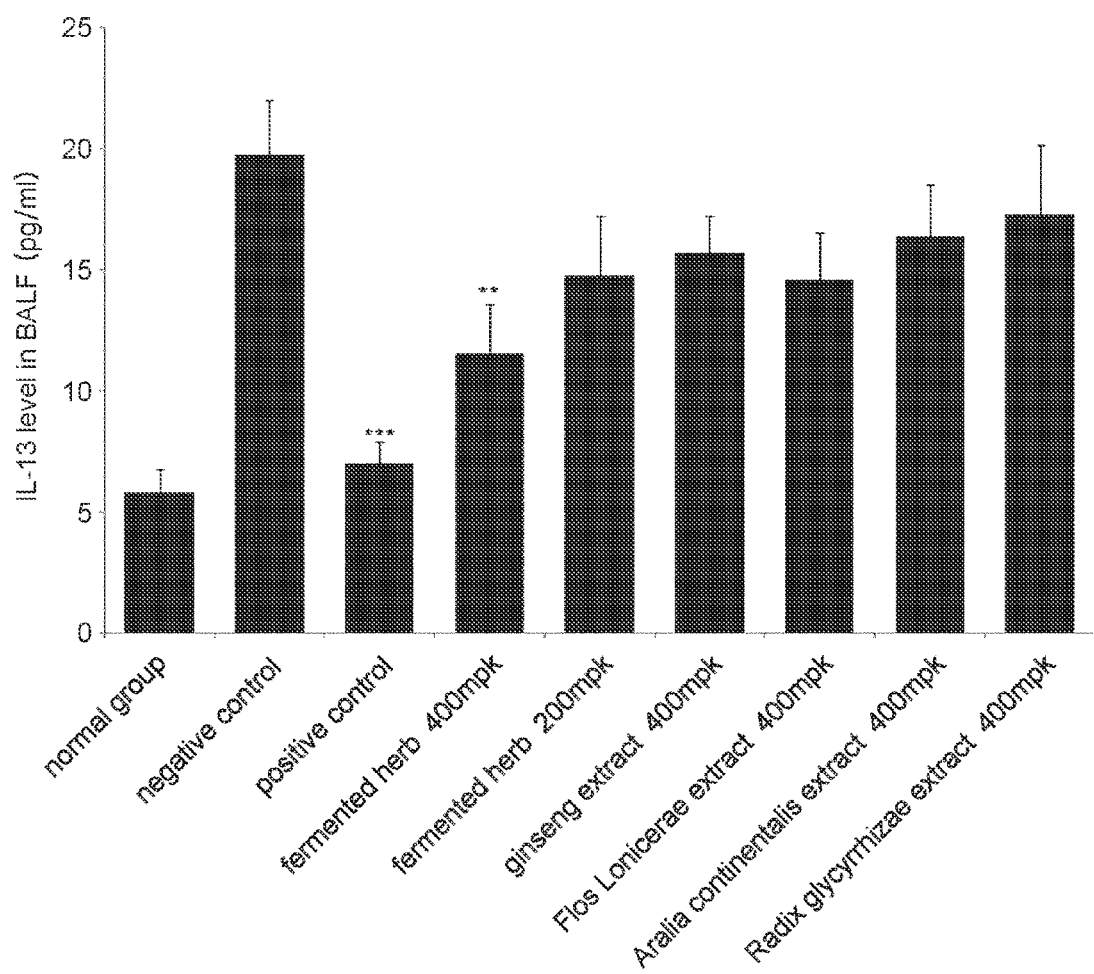
Figure 9:
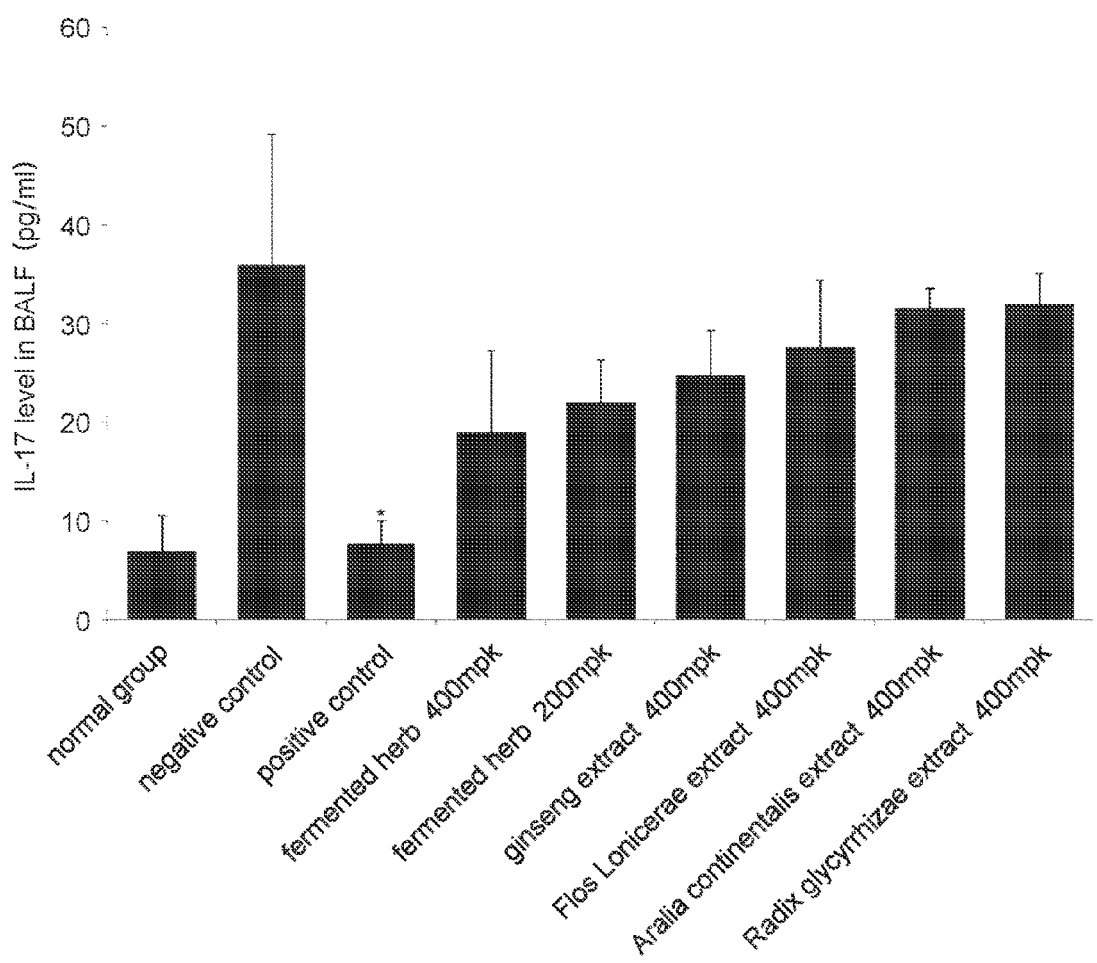

As a result, the level of specific anti-OVA IgE in the normal group was 0.10±0.091 (ng/ml), while it was 23.7±1.89 (ng/ml) in the negative control group sprayed with OVA aerosol for 4 weeks, indicating that the level of specific anti-OVA IgE was increased in the negative control at least 200 times the level of the normal group. In the positive control group treated with CsA (10 mpk), the level of specific anti-OVA IgE in serum was reduced 4 times by the negative control group (p<0.01). In the group treated with 400 mpk of the fermented product of the herbal extract of the present invention, the level of specific anti-OVA IgE was reduced approximately 49.1% by the negative control group (p<0.001). In the group treated with 200 mpk of the fermented product of the herbal extract of the present invention, the level of specific anti-OVA IgE was also reduced, compared with that in the negative control group. In the meantime, in the groups treated with the extracts of ginseng, Flos Lonicerae, *Aralia continentalis*, and Radix glycyrrhizae, the level of specific anti-OVA IgE was reduced, which was not as peculiar as that of the group treated with the fermented product of the herbal extract of the present invention (FIG. 6). Bronchoalveolar lavage fluid (BALF) was isolated and the levels of Th2 cytokines, IL-4 and IL-13, and TH17 cytokine, IL-17, therein were measured. As a result, the levels of IL-4, IL-13, and IL-17 in BALF were increased in the negative control group at least twice the normal group, but decreased in the positive control group treated with 10 mpk of CsA approximately 50% by the negative control group (p<0.001, p<0.05). In the group treated with 400 mpk of the fermented product of the herbal extract of the present invention, the levels of IL-4 (p<0.05) and IL-13 (p<0.01) were all reduced at least 35% by the negative control group. In the group treated with 200 mpk of the fermented product of the herbal extract of the present invention, the levels of those cytokines were all reduced, compared with that in the negative control group. The level of IL-17 was also reduced in the group treated with the fermented product of the herbal extract of the present invention. In the groups treated respectively with the extracts of ginseng, Flos Lonicerae, *Aralia continentalis*, and Radix glycyrrhizae, the levels of IL-4, IL-13, and IL-17 in BALF were all reduced, but not as significant as that of the group treated with the fermented product of the herbal extract of the present invention (FIG. 7~FIG. 9).

Spleen cells were isolated and cultured for 48 hours in the 96 well plate coated with OVA peptide 24 hours before the culture began. The levels of Th1 cytokine IFN-γ, Th2 cytokines IL-4 and IL-13, and Th17 cytokine IL-17 in the supernatant of the spleen cell culture medium were measured. At that time, the normal group plate was not coated with OVA peptide, but the plates of the negative control group, the positive control group, the group treated with the fermented product of the herbal extract of the present invention, and the groups treated with the extracts of ginseng, Flos Lonicerae, *Aralia continentalis*, and Radix glycyrrhizae were all coated with OVA peptide.

Figure 10:
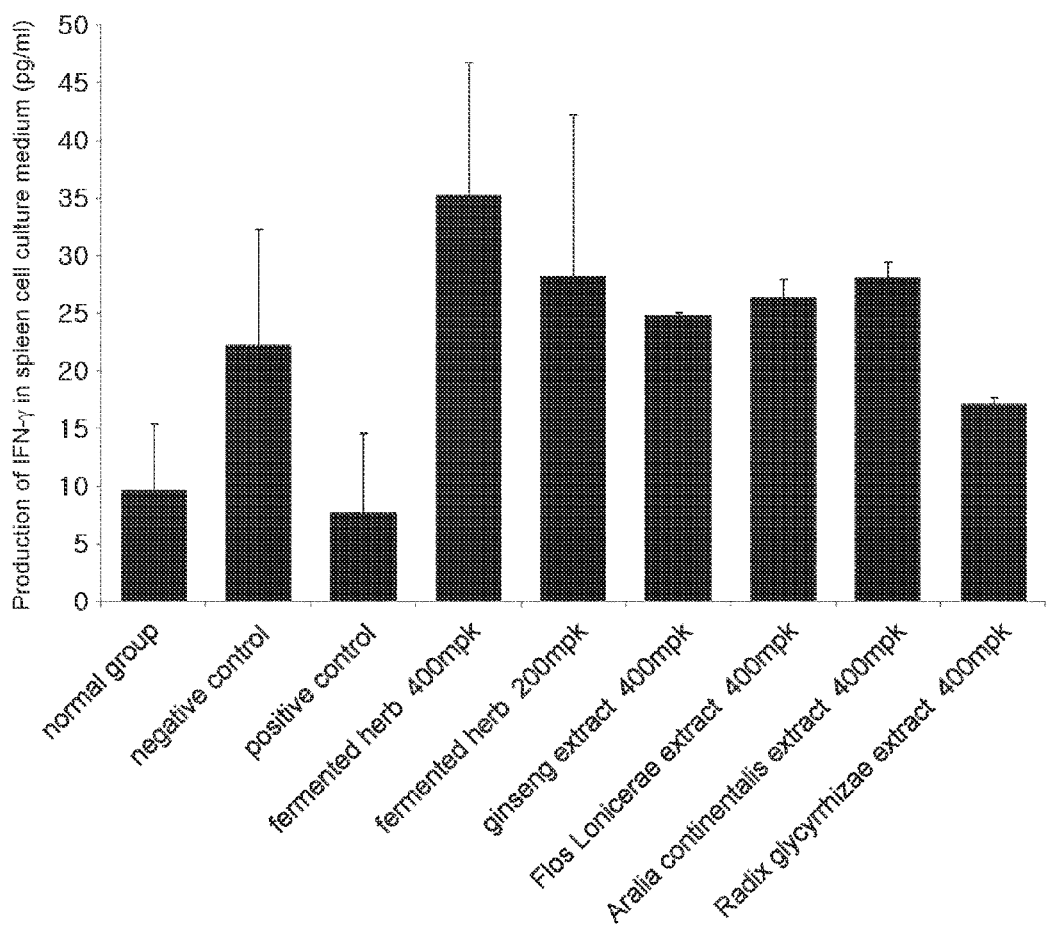
Figure 11:
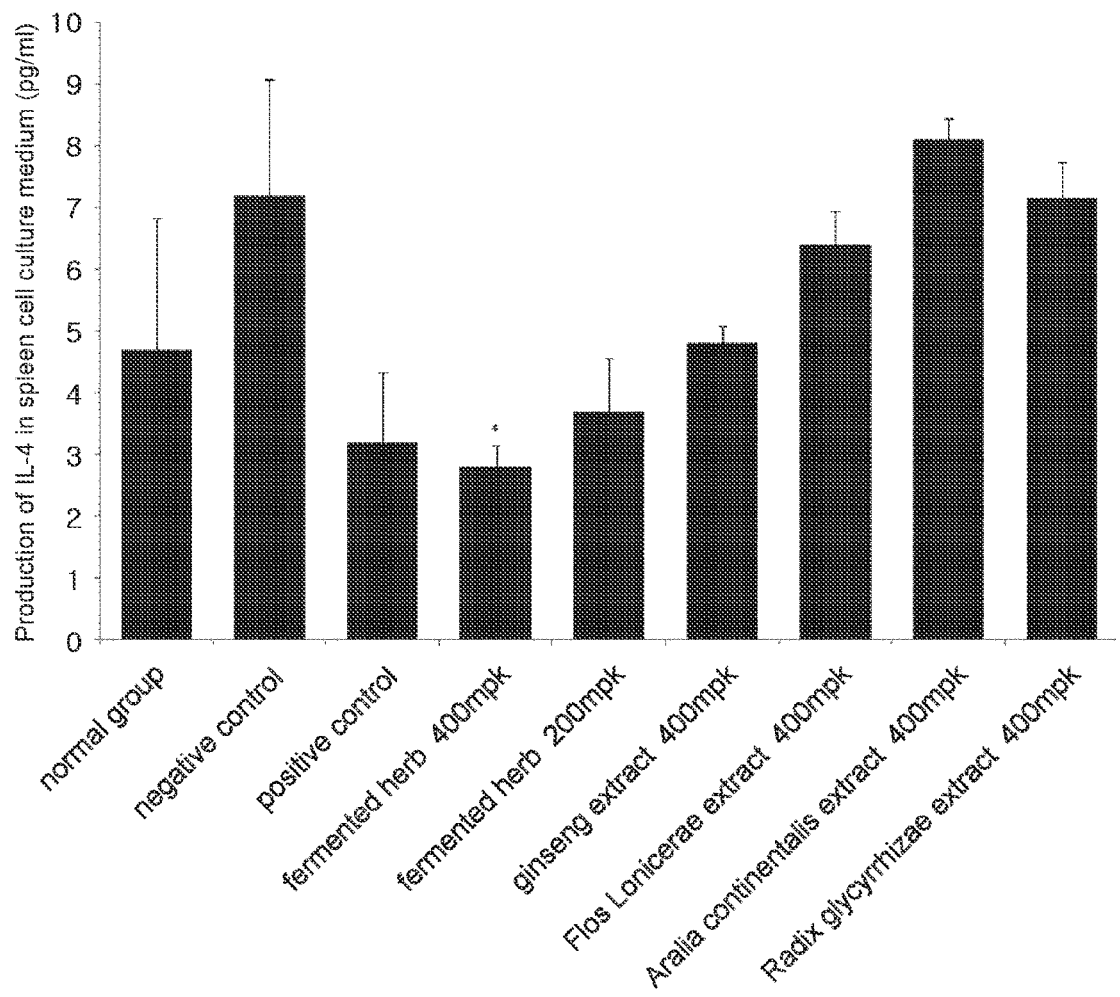
Figure 12:
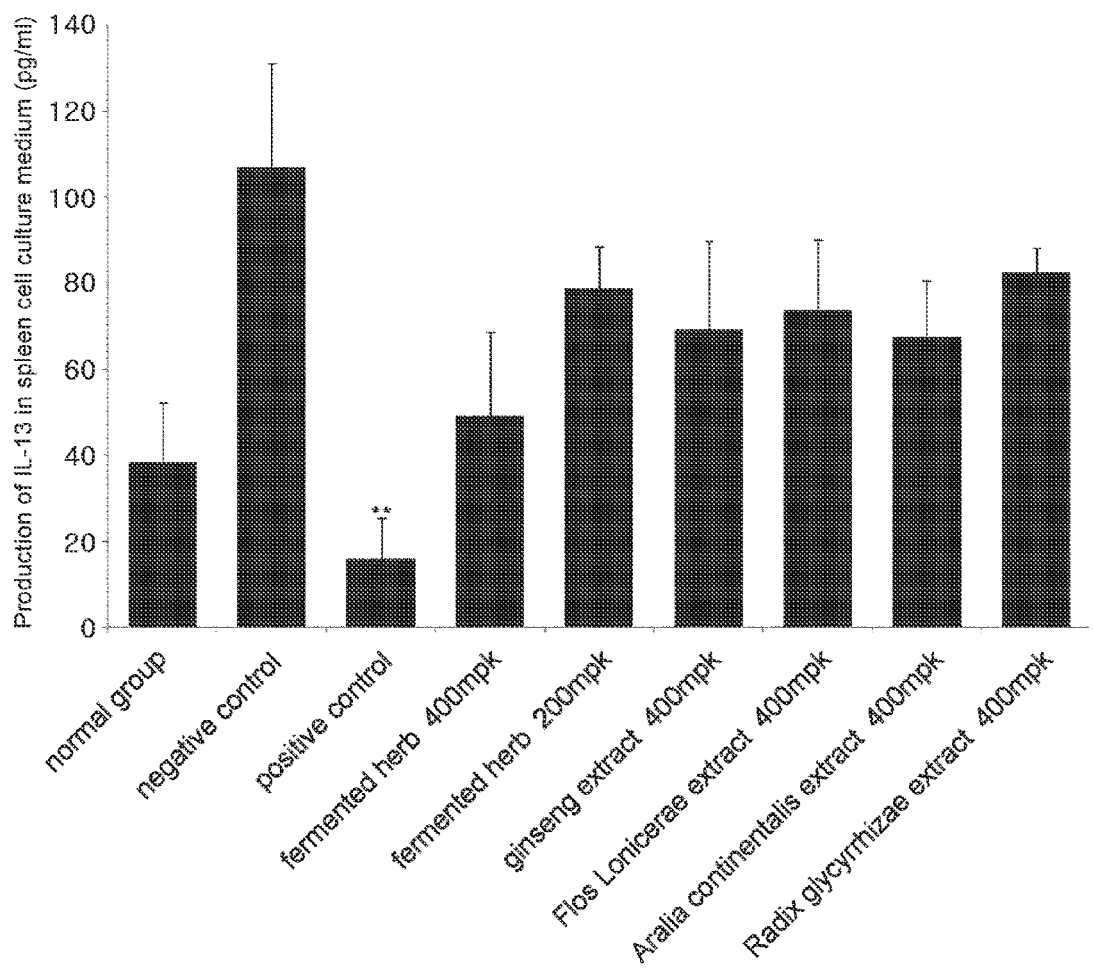
Figure 13:
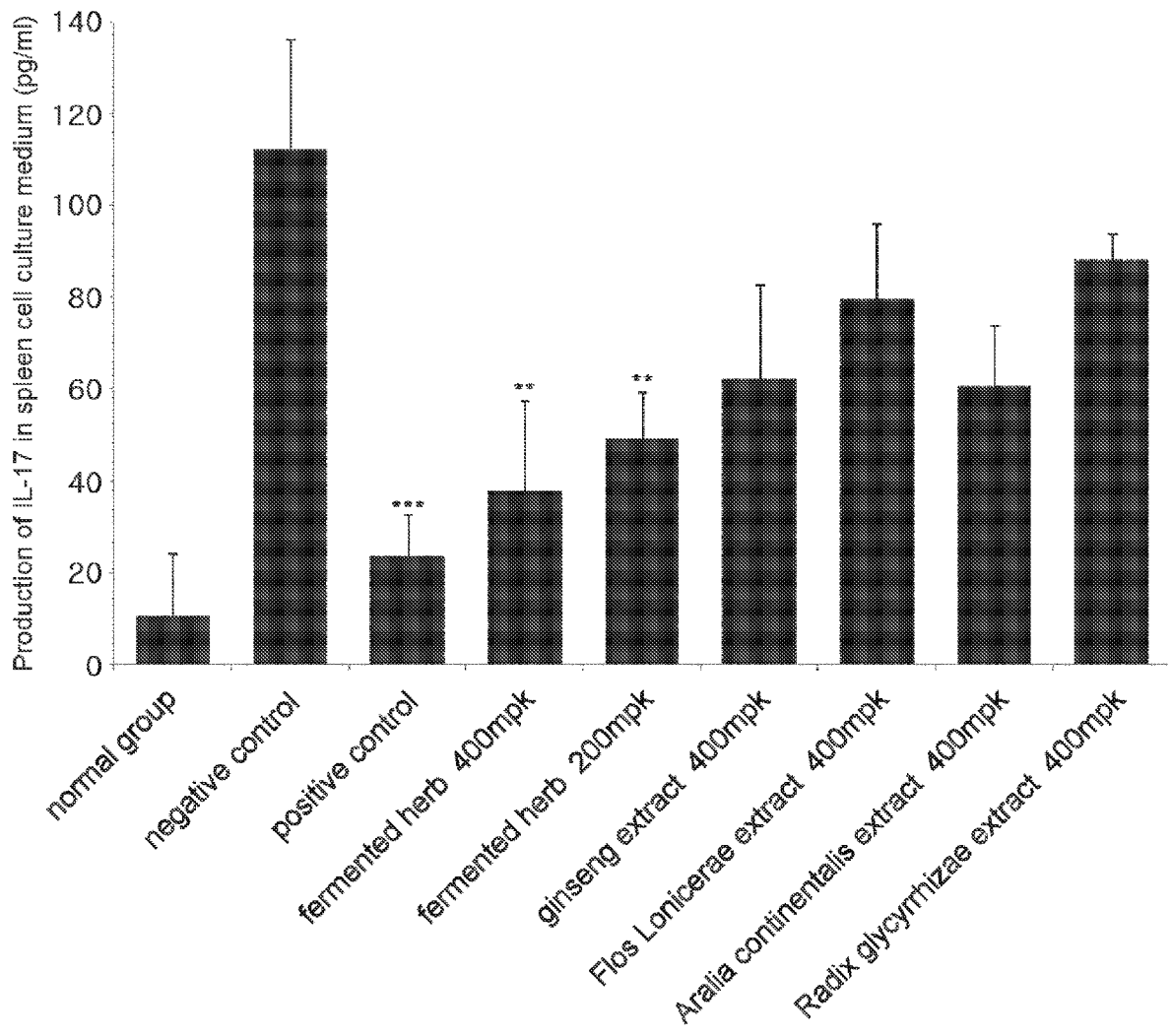

As a result, the levels of IFN-γ in the normal group, the negative control group, and the positive control group treated with CsA were all similar, but the levels were significantly increased in the group treated with the fermented product of the herbal extract of the present invention and the groups treated with the extracts of ginseng, Flos Lonicerae, *Aralia continentalis*, and Radix glycyrrhizae (FIG. 10). In the meantime, the levels of IL-4, IL-13 (p<0.01), and IL-17 (p<0.001) were significantly increased in the negative control group, compared with those of the normal group, but decreased in the positive control group treated with 10 mpk of CsA approximately at least 50% by the negative control group. In the group treated with 400 mpk of the fermented product of the herbal extract of the present invention, the levels of IL-4 (p<0.05), IL-13, and IL-17 (p<0.01) were all reduced about 50% by the negative control group. In the group treated with 200 mpk of the fermented product of the herbal extract of the present invention, the level of IL-17 cytokine was reduced, compared with that in the negative control group (P<0.01). In the groups treated with the extracts of ginseng, Flos Lonicerae, *Aralia continentalis*, and Radix glycyrrhizae, the levels of IL-4, IL-13, and IL-17 were all reduced but not as much as in the group treated with the fermented product of the herbal extract of the present invention (FIG. 11~FIG. 13).

Experimental Example 5

Histopathological Test

The lung was extracted and fixed in 10% formaldehyde solution. The fixed lung was chopped and washed with running water for 8 hours, followed by embedding in epoxy. The epoxy was sliced by using a microtome and the sliced sections were stained with H&E (Hematoxylin & Eosin), M-T and PAS (goblet cell staining) according to standard method. Inflammation and blood cell infiltration around tracheole and alveolar were confirmed by H&E staining and M-T staining. collagen deposition was analyzed by PAS staining.

As a result, in the lung tissues of the negative control group, tracheole and alveolar were severely damaged, inflammatory cells, eosinophils and blood cells were severely infiltrated near AHR (airway hyperresponsiveness), and angiogenesis was observed therein. In addition, collagen deposition was increased around AHR and the AHR got much thicker than that of the normal group, which was almost as thick as being clogged. From the observation from PAS (Periodic Acid-Schiff) staining, it was confirmed that goblet cells (dark pink) were formed a lot near AHR. In the meantime, in the positive control group treated with 10 mpk of CsA, inflammatory cell infiltration around AHR, tracheole and alveolar damage, collagen deposition, and goblet cell infiltration near AHR were significantly inhibited, compared with those of the negative control group. In the group treated with the fermented product of the herbal extract of the present invention, airway resistance and lung injury were suppressed, and the infiltration of inflammatory cells and eosinophils near AHR on lung tissues were also reduced, compared with those of the negative control group. In addition, tracheole and alveolar damage, collagen deposition, and goblet cell infiltration near AHR were significantly inhibited, compared with those of the negative control group. In the groups treated with the extracts of ginseng, Flos Lonicerae, *Aralia continentalis*, and Radix glycyrrhizae, tracheole and alveolar damage in the lung tissues were slightly reduced, but the infiltration of inflammatory cells and eosinophils near AHR was not different from that of the negative control group. Angiogenesis, collagen decomposition observed from M-T staining, and goblet cells around AHR were slightly reduced, compared with those of the negative control group (FIG. 14).

Manufacturing Example 1

Preparation of Pharmaceutical Formulations Containing the Herbal Extract or the Fermented Product Thereof <1-1> Preparation of Syrups Syrups containing the herbal extract or the fermented product thereof of the present invention by 2% (weight/volume) as an effective ingredient were prepared as follows. The herbal extract or the fermented product thereof prepared in Example 1 or Example 2, saccharin and glucose were dissolved in 80 g of warm water. The mixture was cooled down, to which a mixture of glycerin, saccharin, flavors, ethanol, sorbic acid and distilled water was added. Water was added to the mixture, making a total volume of 100 ml.

Composition of the syrup was as follows.

| | |
|---|---|
| Herb extract or fermented product thereof | 2 g |
| Saccharin | 0.8 g |
| Sucrose | 25.4 g |
| Glycerine | 8.0 g |
| Flavor | 0.04 g |
| Ethanol | 4.0 g |
| Sorbic acid | 0.4 g |
| Distilled water | proper amount |

<1-2> Preparation of Tablets

Tablets containing 15 mg of the herbal extract or the fermented product thereof of the present invention as an effective ingredient were prepared as follows.

250 g of the herbal extract or the fermented product thereof prepared in Example 1 or Example 2, 175.9 g of lactose, 180 g of potato-starch and 32 g of colloidal silicic acid were all mixed together. 10% gelatin solution was added to the mixture, which was then pulverized and filtered with 14-mesh sieve. The pulverized mixture was dried, to which 160 g of potato-starch, 50 g of talc and 5 g of magnesium stearate were added to prepare tablets.

| | |
|---|---|
| Herb extract or fermented product thereof | 250 g |
| Lactose | 175.9 g |
| Potato-starch | 180 g |
| Colloidal silicic acid | 32 g |
| 10% gelatin solution | proper amount |
| Potato-starch | 160 g |
| Talc | 50 g |
| Magnesium stearate | 5 g |

Manufacturing Example 2

Preparation of Health Foods Containing the Herbal Extract or the Fermented Product Thereof <2-1> Preparation of Foods Foods containing the herbal extract or the fermented product thereof of the present invention prepared in Example 1 or Example 2 were prepared as follows.

1. Preparation of Spices for Cooking

Health enhancing spices for cooking were prepared with 20~95 weight % of the herbal extract or the fermented product thereof of the present invention according to the conventional method.

2. Preparation of Tomato Ketchup and Sauce

Health enhancing tomato ketchup or sauce was prepared by mixing 0.2~1.0 weight % of the herbal extract or the fermented product thereof of the present invention with tomato ketchup or sauce according to the conventional method.

3. Preparation of Flour Food 0.5~5.0 weight % of the herbal extract or the fermented product thereof of the present invention was added to the flour. Health enhancing foods such as bread, cake, cookies, crackers and noodles were prepared with the flour mixture according to the conventional method.

4. Preparation of Soups and Gravies 0.1~5.0 weight % of the herbal extract or the fermented product thereof of the present invention was added to soups and gravies. Health enhancing meat products, soups and gravies were prepared with this mixture by the conventional method.

5. Preparation of Ground Beef

Health enhancing ground beef was prepared by mixing 10 weight % of the herbal extract or the fermented product thereof of the present invention with ground beef according to the conventional method.

6. Preparation of Dairy Products

5~10 weight % of the herbal extract or the fermented product thereof of the present invention was added to milk. Health enhancing dairy products such as butter and ice cream were prepared with the milk mixture according to the conventional method.

7. Preparation of Sun-Sik

Brown rice, barley, glutinous rice and Yulmu (Job's tears) were gelatinized according to the conventional method, dried and pulverized to obtain 60-mesh powders. Black soybean, black sesame and wild sesame were steamed and dried according to the conventional method and pulverized to obtain 60-mesh powders. The herbal extract or the fermented product thereof of the present invention was concentrated under reduced pressure, spray-dried and pulverized to obtain 60-mesh dry powders. Sun-Sik was prepared by mixing the dry powders of the grains, seeds and the herbal extract or the fermented product thereof of the present invention according to the below ratio.

Grains (brown rice: 30 weight %, Yulmu: 15 weight %, barley: 20 weight %),

Seeds (wild sesame: 7 weight %, black soybean: 8 weight %, black sesame: 7 weight %), Dry powders of the herbal extract or the fermented product thereof of the present invention (3 weight %),

*Ganoderma lucidum* (0.5 weight %),

*Rehmannia glutinosa* (0.5 weight %)

<2-2> Preparation of Beverages

1. Preparation of Carbonated Beverages

Syrup was prepared by mixing the herbal extract or the fermented herb extract of the present invention with sugar (5~10%), citric acid (0.05~0.3%), caramel (0.005~0.02%) and vitamin C (0.1~1%). The syrup was sterilized at 85~98° C. for 20~180 seconds, and then mixed with cooling water at the ratio of 1:4. Carbon dioxide was injected thereto by 0.5~0.82% to prepare carbonated beverages containing the herbal extract or the fermented product thereof of the present invention.

2. Preparation of Health Beverages

The herbal extract or the fermented product thereof of the present invention (0.5%) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

3. Preparation of Vegetable Juice

Health enhancing vegetable juice was prepared by adding 5 g of the herbal extract or the fermented product thereof of the present invention to 1,000 and of tomato or carrot juice according to the conventional method.

4. Preparation of Fruit Juice

Health enhancing fruit juice was prepared by adding 1 g of the herbal extract or the fermented product thereof of the present invention to 1,000 and of apple or grape juice according to the conventional method.

What is claimed is:

1. A method for treating a respiratory disease, comprising administering to a subject in need thereof a pharmaceutical composition comprising a therapeutically effective amount of an extract from a mixture of herbs, wherein the herbs comprise *Sophora flavascens*, Radix glycyrrhizae, Flos lonicerae, Angelicae Gigantis radix, *Aralia continentalis*, *Inula hele-* nium, Saposhnikoviae radix, *Zizyphus spinosa, Houttuynia cordata,* Forsythiae fructus, *Arctium lappa,* Herba epimedii, ginseng, Lithospermi radix, Sancjuisorbae radix, Cnidii rhizoma, Scrophulariae radix, and Polygoni cuspidati radix, and wherein the extract is (i) an aqueous extract; (ii) an organic solvent extract; (iii) a preparation made by fermenting the aqueous extract with one or more lactic acid bacteria, and isolating or separating the medium from the grown culture to yield the preparation; or (iv) a preparation made by drying the organic solvent extract to yield solids, dissolving the solids in water, fermenting the redissolved solids with one or more lactic acid bacteria, and isolating or separating the medium from the grown culture to yield the preparation.

2. The method according to claim 1, wherein the herbal extract is extracted by hot-water extraction from the herb mixture comprising 10 weight parts of *Sophora flavescens*, 2~8 weight parts of Radix glycyrrhizae, 2~8 weight parts of Flos Lonicerae, 2~8 weight parts of Angelicae Gigantis radix, 2~8 weight parts of *Aralia continentalis,* 2~8 weight parts of *Inula helenium,* 2~8 weight parts of Saposhnikoviae radix, 2~8 weight parts of *Zizyphus spinosa,* 5~15 weight parts of *Houttuynia cordata,* 2~8 weight parts of Forsythiae fructus, 5~15 weight parts of *Arctium lappa,* 2~8 weight parts of Herba epimedii, 5~15 weight parts of ginseng, 2~8 weight parts of Lithospermi radix, 2~8 weight parts of Sanguisorbae radix, 2~8 weight parts of Cnidii rhizoma, 5~15 weight parts of Scrophulariae radix, and 2~8 weight parts of Polygoni cuspidati radix.

3. The method according to claim 1, wherein the organic solvent is selected from the group consisting of $C_1$~$C_4$ alcohols, acetone, and the aqueous solutions thereof.

4. The method according to claim 1, wherein the one or more lactic acid bacteria are selected from the group of genera consisting of *Lactobacillus* sp., *Bifidobacterium* sp., *Streptococcus* sp., *Leuconostoc* sp., *Pediococcus* sp., and *Lactococcus* sp.

5. The method according to claim 4, wherein the lactic acid bacterium or one of the lactic acid bacteria is *Lactobacillus rhamnosus.*

6. The method according to claim 1, wherein, in the fermentation of the aqueous extract or redissolved solids, the lactic acid bacteria are inoculated at the concentration of 0.5-5 weight % by the total weight of the sample.

7. The method according to claim 1, wherein, in the fermentation of the aqueous extract or redissolved solids, the lactic acid bacteria are fermented at the temperature of 20-40° C. for 24-52 hours.

8. The method according to claim 1, wherein the respiratory disease is selected from the group consisting of asthma, bronchiectasis, chronic obstructive pulmonary disease, and chronic cough.

* * * * *